United States Patent
Biering et al.

(10) Patent No.: US 7,160,846 B2
(45) Date of Patent: Jan. 9, 2007

(54) AQUEOUS CONCENTRATE FOR THE DISINFECTION OF SURFACES

(75) Inventors: Holger Biering, Grevenbroich (DE); Faubel Heiko, Wermelskirchen (DE); Rudolf Glasmacher, Monheim (DE); Veronika Heide, Dormagen (DE)

(73) Assignee: Ecolab Inc., St. Paul, MN (US)

(*) Notice: Subject to any disclaimer, the term of this patent is extended or adjusted under 35 U.S.C. 154(b) by 68 days.

(21) Appl. No.: 10/518,422

(22) PCT Filed: Jun. 13, 2003

(86) PCT No.: PCT/EP03/06274

§ 371 (c)(1),
(2), (4) Date: Mar. 9, 2005

(87) PCT Pub. No.: WO04/000373

PCT Pub. Date: Dec. 31, 2003

(65) Prior Publication Data

US 2005/0176618 A1 Aug. 11, 2005

(30) Foreign Application Priority Data

Jun. 22, 2002 (DE) ............................... 102 27 872

(51) Int. Cl.
*C11D 1/62* (2006.01)
*C11D 3/26* (2006.01)
*C11D 3/37* (2006.01)

(52) U.S. Cl. ................ 510/214; 510/199; 510/238; 510/384; 510/386; 510/391; 510/475; 510/477; 510/499; 510/501; 510/504

(58) Field of Classification Search ................. None
See application file for complete search history.

(56) References Cited

U.S. PATENT DOCUMENTS

| | | | |
|---|---|---|---|
| 4,661,523 A | 4/1987 | Disch et al. | |
| 5,929,016 A | 7/1999 | Harrison | |
| 6,090,768 A * | 7/2000 | Delaney et al. | 510/325 |
| 6,258,368 B1 | 7/2001 | Beerse et al. | |
| 6,358,903 B1 * | 3/2002 | Hopkinson et al. | 510/375 |
| 2003/0008795 A1 * | 1/2003 | Sidoti | 510/283 |

FOREIGN PATENT DOCUMENTS

| | | |
|---|---|---|
| DE | 10054020 | 5/2002 |
| EP | 1126014 | 8/2001 |
| FR | 2622397 | 5/1989 |
| WO | WO94/27436 | 12/1994 |
| WO | WO98/56886 | 12/1998 |

* cited by examiner

*Primary Examiner*—Gregory R. Del Cotto
(74) *Attorney, Agent, or Firm*—Andrew D. Sorensen; Anneliese S. Mayer

(57) ABSTRACT

The invention relates to the field of cleaning and disinfection of hard surfaces. The cleaning and disinfection of the surfaces is achieved by means of a deaning textile and an aqueous preparation, comprising disinfection agents and additives selected from a group comprising a quaternary ammonium compound of formula (II), polydialkyldiallylammonium salts and derivatives thereof and the copolymers of dialkyldiallylammonium salts with acrylamide, and/or acrylic acid, and/or vinyl acetate, and derivatives thereof. The invention further relates to an aqueous concentrate, an aqueous preparation produced therefrom and a method for the reduction of active ingredient losses in disinfection solutions when using said concentrate.

6 Claims, No Drawings

AQUEOUS CONCENTRATE FOR THE DISINFECTION OF SURFACES

This invention relates generally to the cleaning and disinfection of hard surfaces. The surfaces are cleaned and disinfected with a cleaning textile and a water-based preparation containing disinfectants and additive. More particularly, the invention relates to a water-based concentrate, to a water-based preparation made up therefrom and to a process for reducing the loss of active substance from disinfectant solutions using the concentrate.

The cleaning and care of surfaces is necessary in hygienically particularly demanding areas. Adhering microorganisms are largely eliminated at regular intervals in the process. Particularly high standards have to be applied, for example, in the food industry and large kitchens, but particularly in the medical field, above all in general practices and hospitals. In order to make cleaning and disinfection particularly efficient, there has been no shortage of attempts to optimize them.

DE 199 18 475 A1 discloses a process for the disinfecting care of floors. The problem addressed by that invention was to combine the amine-based broad-spectrum antimicrobial agents with the cleaning and care of floors in one process with no loss of effectiveness which had never been achieved before. In the practical application of this process, the floors are wiped with a dilute water-containing preparation. Wiping can be carried out with soft, preferably absorbent articles, for example brushes, cloths, mops and sponges, either by hand or with suitable machines. The application of the dilute water-based preparation consisting of disinfectant and cleaner may even be carried out separately from the subsequent wiping step, for example by spraying on. Where more intensive cleaning is required, relatively large quantities of water-based preparation may first be applied and the excess quantities may be taken up again from the floor with the soil removed after wiping. The quantity of water-based preparation remaining on the floor is left to dry to form the required floor-care film on the cleaned and disinfected surface.

However, greater demands are imposed on the disinfection of floors and hard surfaces, particularly in hospitals and elsewhere in the medical field, on account of the stricter hygiene regulations. Processes which ensure that germs cannot be carried over by using the same cleaning cloths in different rooms are now being successfully used in those areas. Proven processes are in particular the two-mop process and the one-mop process. In the two mop process, a defined quantity of disinfectant per unit area is manually applied and spread with the first mop and the excess liquid is taken up with a second mop.

In the one-mop process, the cleaning mop is briefly immersed in the disinfecting solution, excess disinfectant is squeezed out and the disinfecting cleaning step is carried out with the damp mop. Both processes guarantee a high level of hygiene because the cleaning textiles are only used in one room, are subsequently set aside as used mops and then subjected to disinfecting washing.

Unfortunately, both the described processes are very labor-intensive so that simpler variants are being sought. A more favorable process of this type is a modification of the one-mop process in which several mops are placed in the disinfecting solution at the beginning of work and are used as required. Since this process involves far less work, it is being widely adopted, particularly in hospitals.

However, testing of the disinfectant concentrations in this process has shown that the concentration of disinfectant in the cleaning solution decreases considerably with time. It has been found that, after the cleaning textiles have been placed in the disinfecting solution, disinfecting agents are adsorbed onto the relatively large surface of the cleaning textiles through the prolonged contact of the cleaning textiles not used immediately with the disinfecting solution. This adsorption of the disinfecting agents onto the cleaning textiles depends upon the particular type of textile and upon the nature of the disinfectants. However, it has been found that, on average, most cleaning textiles show such adsorption. Accordingly, it is possible for only a fraction of the disinfecting agent to be present in the in-use solution after a certain time, with the result that the cleaning solution no longer has an adequate disinfecting effect after a certain time. In addition, even if sufficient adsorbed disinfectant is still present on the surface of the particular textile used for cleaning, it can only be applied to the surfaces to be disinfected to a small extent, if at all, because it is adsorbed onto the textile and cannot be transferred. These effects result in incomplete disinfection of the surfaces to be treated so that the necessary hygiene requirements are not satisfied.

The problem addressed by the present invention was to avoid the disadvantages of the prior art and to provide a water-based concentrate where the antimicrobial agents present in dilute solutions of the concentrate would no longer be adsorbed onto cleaning textiles to the same extent as with known disinfectant solutions. This would above all enable cleaning textiles to be stored before use in disinfecting solutions and better utilization of the antimicrobial agents used to be guaranteed for the application originally intended for them, namely disinfection.

The problem stated above has been solved by a water-based concentrate containing a) 5 to 30% by weight and preferably 10 to 25% by weight of an antimicrobial agent selected from the group of aldehydes, aldehyde derivatives, phenols, phenol derivatives, amides, amide derivatives, amines, amine derivatives, quaternary ammonium compounds corresponding to formula (I):

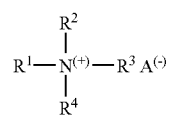

(I)

where $R^1$ is an alkyl group containing 6 to 16 carbon atoms, $R^2$ is an alkyl group containing 1 to 12 carbon atoms or a benzyl group, $R^3$ and $R^4$ are alkyl groups containing 1 to 4 carbon atoms or hydroxyalkyl groups containing 2 to 4 carbon atoms and $A^{(-)}$ is a halide, methoxysulfate or methoxyphosphate anion, and b) 5 to 50% by weight and preferably 10 to 30% by weight of an additive selected from the group of quaternary ammonium compounds corresponding to formula (II):

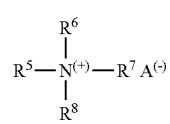

(II)

where $R^5$ and $R^6$ are alkyl groups containing 16 to 22 carbon atoms or groups with the formula $R^9CO$ $(XC_nH_{2n})_a$ where $R^9CO$ is a linear acyl group containing 16 to 22 carbon atoms, X is oxygen or —NH—, n =2 or 3, a=1 to 4, $R^7$ has the same meaning as $R^5$ and $R^6$ or is an alkyl group containing 1 to 4 carbon atoms and $R^8$ is an alkyl group containing 1 to 4 carbon atoms or a hydroxyalkyl group containing 2 to 4 carbon atoms and $A^{(-)}$ is a halide, methoxysulfate or methoxyphosphate anion, polydialkyl diallyl ammonium salts and derivatives thereof, copolymers of dialkyldiallyl ammonium salts with acrylamide and/or acrylic acid and/or vinyl acetate and derivatives thereof.

A major advantage of the concentrate according to the invention is that it counteracts the reduction in concentration of the antimicrobial agent mentioned in disinfectant solutions that are intended to be taken up by cleaning textiles and subsequently used for surface disinfection. This effect is in evidence particularly clearly when the contact between disinfectant solutions and cleaning textiles is prolonged (as, for example, in storage).

Cleaning textiles in the context of the invention are any auxiliaries which, for disinfecting surfaces, are contacted first with the disinfecting solution and then with the surface to be disinfected. Such auxiliaries may be cloths, rags or nonwovens. However, sponges and brushes may also be used. A preferred embodiment is a wiping mop with readily replaceable heads. The cleaning textiles may be made of fibers of native origin, for example cotton. However, synthetic fibers, for example microfibers, may also be used. Basically, polymer-coated cleaning textiles are also suitable.

The effect of the present invention is surprisingly achieved with the above-mentioned antimicrobial agents which have already been repeatedly used. Within the group of aldehydes, formaldehyde, glyoxal, glutaraldehyde and other derivatives of aldehydes are particularly suitable. Another important group of antimicrobial agents are the above-mentioned phenols and phenol derivatives and the quaternary ammonium compounds corresponding to formula (I), of which those where dimethyl didecyl ammonium and/or dimethyl dioctyl ammonium and/or benzalkonium are present as the cationic component are particularly preferred.

Other antimicrobial agents suitable for the purposes of the invention are amines and amine derivatives.

In a particularly advantageous embodiment, the above-mentioned aminofunctional antimicrobial agent is selected from alkylamines corresponding to formulae (III) and/or (IV):

$R^{10}$—NH—$(CH_2)_3NH_2$      (III),

$R^{10}$—N—$[(CH_2)_3NH_2]_2$      (IV), where $R^{10}$ is a $C_{8-18}$ and preferably $C_{12-14}$ alkyl group, which may be present in unneutralized or partly or completely neutralized form, and/or active substances obtainable by reacting a propylenediamine corresponding to formula (III):

$R^{10}$—NH—$(CH_2)_3NH_2$      (III)

with glutamic acid or glutamic acid derivatives corresponding to formula (V):

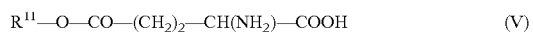
$R^{11}$—O—CO—$(CH_2)_2$—CH($NH_2$)—COOH      (V)

where $R^{11}$ is hydrogen or a $C_{1-4}$ alkyl group, and optionally reacting the resulting product with ethylene oxide and/or propylene oxide, optionally followed by further reaction with organic or inorganic acids.

Amides also belong to the class of antimicrobial agents according to the present invention. The pyrrolidone carboxylic acid amides and their salts obtainable, for example, by the above-mentioned reaction of amines stand out here in their importance. Particular emphasis is placed on the reaction products of glutamic acid with alkyl propylenediamines which are also known commercially as Glucoprotamin®.

It is obvious that the advantages of the concentrates according to the invention are also obtained when several of the above-mentioned and/or additional antimicrobial agents are present alongside one another in the concentrates according to the invention.

In a particularly preferred embodiment, the components of formula (II) mentioned as additive in the concentrates according to the invention are selected from the group of difatty acid trialkanolamine ester salts which are also known as esterquats. These quaternary ammonium compounds correspond to general formula (VI):

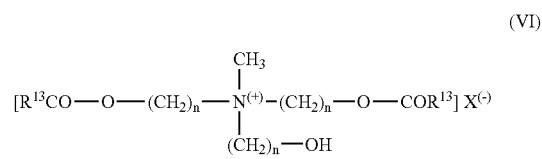

(VI)

where $R^{13}CO$ is an aliphatic acyl group containing 12 to 22 carbon atoms and 0, 1, 2 or 3 double bonds, n=2 or 3 and X is halide, methoxysulfate or methoxyphosphate.

As already mentioned, the additive present in the concentrate in accordance with the invention preferably also contains cationic polymers. These may be, on the one hand, poly(dialkyldiallylammonium salts) or derivatives thereof or copolymers of dialkyldiallylammonium salts with acrylamide and/or acrylic acid and/or vinyl acetate and derivatives thereof. In one particular embodiment, the poly(dimethyldialkylammonium)chloride or a copolymer of dimethyldiallyl ammonium chloride with acrylamide and/or acrylic acid and/or vinyl acetate or derivatives of copolymers of dimethyldiallyl ammonium chloride with acrylamide and/or acrylic acid and/or vinyl acetate is/are used. Examples of these compounds are the cationic polymers marketed by Chemviron under the name of Merquat.

All the additives listed here may be used either individually or in the form of mixtures to solve the problem addressed by the invention.

Preferred additional formulation ingredients are, in particular, oil sulfonates, fatty alcohol sulfates, fatty acid condensation products, alkyl polyglycol ethers and alkylaryl polyglycol ethers or mixtures thereof.

In a preferred embodiment, the water-based concentrate may contain other auxiliaries and additives from the groups of surfactants, flow controllers, complexing acids, acids, organic solvents, solubilizers, dyes, perfumes and mixtures thereof.

The disinfecting solutions typically used in practice may be prepared from the concentrates according to the invention, for example, by simple dilution with water. However, it is specifically pointed out that the aqueous disinfecting solutions required may also be obtained without using the concentrate. Accordingly, the present invention also encompasses embodiments where the disinfecting solutions used in practice are prepared in other ways. For example, the components a) (antimicrobial agent) and b) (additive) present in the concentrate according to the invention may be individually diluted and then combined or one of the components may be diluted and the other added in concentrated form. The required aqueous disinfecting solutions can also be obtained in this way and optionally by other known methods.

Accordingly, the present invention also relates to a water-containing preparation which corresponds in its composition to a disinfecting solution obtainable by diluting the concentrate according to the invention with water in a ratio of 1:10 to 1:400, preferably in a ratio of 1:20 to 1:200 and more particularly in a ratio of 1:30 to 1:100.

In a preferred embodiment, the above-mentioned antimicrobial agent and//or the above-mentioned additive may be separately added to an existing aqueous solution in such a quantity that the water-containing preparation ultimately present contains as much of the antimicrobial agent and the additive as it does where the concentrate is diluted in the ratios mentioned above. However, the problem addressed by the invention can also be solved by using the additive and the aqueous preparation of the antimicrobial agent spatially separately from one another.

Accordingly, the present invention also relates to a process for treating cleaning textiles in surface disinfection in which the cleaning textile is treated first with one or more of the additives mentioned in connection with the concentrate according to the invention in dilute or undiluted form and then with the water-containing preparation according to the invention. This process is preferably used to reduce the loss of disinfectant from the water-containing preparation. It is pointed out by way of explanation at this juncture that an aqueous preparation in the context of the present invention is the same as a disinfecting solution.

In other words, in the process according to the invention, the cleaning textile is treated first with one or more additives in dilute or undiluted form, the additive(s) being selected from the group of the group of quaternary ammonium compounds corresponding to formula (II):

where $R^5$ and $R^6$ are alkyl groups containing 16 to 22 carbon atoms or groups with the formula $R^9CO(XC_nH_{2n})_a$, where $R^9CO$ is a linear acyl group containing 16 to 22 carbon atoms, X is oxygen or —NH—, n=2 or 3, a=1 to 4, $R^7$ has the same meaning as $R^5$ and $R^6$ or is an alkyl group containing 1 to 4 carbon atoms and $R^8$ is an alkyl group containing 1 to 4 carbon atoms or a hydroxyalkyl group containing 2 to 4 carbon atoms and $A^{(-)}$ is a halide, methoxysulfate or methoxyphosphate anion, polydialkyl diallyl ammonium salts and derivatives thereof, copolymers of dialkyldiallyl ammonium salts with acrylamide and/or acrylic acid and/or vinyl acetate and derivatives thereof, and then with the water-containing preparation according to the invention.

In one embodiment, for example, the cleaning textile may first be treated with a solution of the above-mentioned additive. This may be done, for example, by immersing the cleaning textile in a pretreatment solution of the additive. If desired, the cleaning textile may be dried after immersion. If a cleaning textile thus pretreated is then immersed in a water-containing preparation according to the invention, the antimicrobial agent present in the water-containing preparation according to the invention is no longer absorbed by the cleaning textile to the extent it would be without corresponding pretreatment. This results in the considerable advantage in terms of practical application that only a slight reduction, if any, in the effectiveness of the disinfecting solution is observed during prolonged storage of cleaning textiles in disinfecting solutions.

In a preferred embodiment of the process according to the invention, the additive(s) mentioned make up a total concentration in the pretreatment of 0.01 to 10% by weight, preferably 0.05 to 1% by weight and more particularly 0.075 to 0.15% by weight, based on the pretreatment solution.

The present invention also relates to a system comprising at least two preparations, at least one preparation containing one or more antimicrobial agents selected from the antimicrobial agents to be used in the concentrate according to the invention and at least one other preparation containing one or more additives selected from the additives to be used in the concentrate according to the invention.

The following Examples are intended to illustrate the invention without limiting it in any way.

EXAMPLES

Various aqueous disinfecting solutions were used for the Examples. Besides other formulation ingredients not crucial to the invention, solution E1 contained ca. 0.05% by weight of glutaraldehyde and ca. 0.1% by weight of glyoxal—based on the solution as a whole—as antimicrobial agents. Besides other formulation ingredients not crucial to the invention, solution E2 contained ca. 0.15% by weight of benzalkonium chloride, ca. 0.02% by weight of 2-phenylphenol and ca. 0.02% by weight of polyhexamethylene biguanidinium chloride—based on the solution as a whole—as antimicrobial agents. Besides other formulation ingredients not crucial to the invention, solution E3 contained ca. 0.13% by weight of Glucoprotamin® (a product of Ecolab GmbH & Co. OHG) and ca. 0.01 % by weight of phenoxyethanol—based on the solution as a whole—as antimicrobial agents.

A Polyfix® cloth, which consists of a polyurethane-impregnated viscose/nonwoven matrix, and a Polyfix® Microclean cloth, which consists of a microfiber, were used as the cleaning textiles. Both cleaning textiles are products of Ecolab GmbH & Co. OHG. Poly(dimethyldiallylammonium chloride) commercially obtainable as Polyquat® 40 was used as the additive.

The cleaning textiles were conventionally washed with a typical laundry detergent at 60° C. in a standard washing machine.

In the test according to the invention, in contrast to the normal wash program, 3.0 g/l of Polyquat® 40 (additive) was added in the final rinse cycle of the washing machine which was otherwise carried out with water only. After drying, the cloths were dried for 3 h at room temperature. The cloths folded 8 times were then immersed for 60 mins. in the particular disinfecting solutions. Thereafter the cleaning textile was wrung out by the same person under the same conditions and the resulting solution was collected. The loss of disinfectant in the resulting solution was then determined.

The results of the tests are set out in Table 1. By way of explanation, it is pointed out that the extent to which the disinfectant concentration freely available after the 60-minute immersion of the cloths differs from the concentration present in the particular disinfecting solution at the beginning of the tests was determined in the tests. The result is expressed in the Table as the percentage difference, the starting disinfectant concentration being put at 100%.

TABLE 1

Loss of disinfectant from disinfecting solutions under different conditions

| Disinfecting solution | Loss of disinfectant with Polyfix ® Microclean cloth | | Loss of disinfectant with Polyfix ® cloth | |
|---|---|---|---|---|
| | No addition in final rinse cycle | Polyquat ® 40 added in final rinse cycle | No addition in the final rinse cycle | Polyquat ® 40 added in the final rinse cycle |
| E1 | 31% | 5% | 31% | 9% |
| E2 | 56% | 23% | 31% | 12% |
| E3 | 30% | 9% | 35% | 8% |

The effect which the use of the additive has is clear from Table 1. Irrespective of the nature of the cleaning textile and the disinfectant, the loss of disinfectant in the disinfecting solution collected was clearly reduced by addition of the additive.

Similar results are also achieved where the antimicrobial agent and additive are present in one and the same solution.

The invention claimed is:

1. A method of disinfecting a floor comprising:
   a) applying to a cleaning mop an additive in dilute or undiluted form, the additive selected from the group consisting of a polydialkyl diallyl ammonium salt, and derivatives thereof copolymers of dialkyl diallyl ammonium salts, with acylamide and/or acrylic acid and/or vinyl acetate and derivatives thereof a quaternary ammonium compound having the formula:

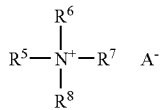

where $R^5$ and $R^6$ are alkyl groups containing 16 to 22 carbon atoms or groups with the formula $R^9CO(XC_nH_{2n})_a$ where $R^9CO$ is a linear acyl group containing 16 to 22 carbon atoms, X is oxygen or —NH—, n=2 or 3 , a=1 to 4, $R^7$ has the same meaning as $R^5$ and $R^6$ or is an alkyl group containing 1 to 4 carbon atoms and $R^8$ is an alkyl group containing 1 to 4 carbon atoms or a hydroxyalkyl group containing 2 to 4 carbon atoms and $A^{(-)}$ is a halide, methoxysulfate or methoxyphosphate anion, and mixtures thereof; and thereafter b) applying to the cleaning mop an aqueous floor disinfecting composition comprising:
      i) water and an antimicrobial agent selected from the group consisting of aldehydes, aldehydes derivatives, phenols, phenol derivatives, amides, amide derivatives, amines, and quaternary ammonium compounds having the formula:

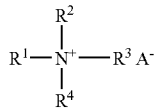

where $R^1$ is an alkyl group containing 6 to 16 carbon atoms, $R^2$ is an alkyl group containing 1 to 12 carbon atoms or a benzyl group, $R^3$ and $R^4$ are alkyl groups containing 1 to 4 carbon atoms or hydroxyalkyl groups containing 2 to 4 carbon and $A^{(-)}$ is a halide, methoxysulfate or methoxyphosphate anion, and further wherein the antimicrobial agent present in the aqueous floor disinfecting composition is not adsorbed onto the cleaning mop to the extent it would be without first treating with the additive; and
   c) applying the disinfecting composition to a floor using the cleaning mop.

2. The method of claim 1, wherein the antimicrobial agent is selected from the group consisting of formaldehyde, glutaraldehyde, glyoxal, dimethyl didecyl ammonium compounds, dimethyl dioctyl ammonium compounds, benzalkonium ammonium compounds, alkylamines having the formula:

$$R^{10}—NH—(CH_2)_3NH_2,$$

alkylamines having the formula:

$$R^{10}—NH—[(CH_2)_3NH_2]_2,$$

where R10 is a $C_{8-18}$ alkyl group, and
the reaction product of glutamic acid with alkyl propylenediamine.

3. The method of claim 1, the floor disinfecting composition further comprising other additives selected from the group consisting of surfactants, flow controllers, complexing acids, acids, organic solvents, solubilizers, dyes, perfumes, and mixtures thereof.

4. The method of claim 1, wherein the cleaning mop is a cloth, rag, nonwoven, sponge, or brush material.

5. The method of claim 1, wherein the cleaning mop is made of cotton, or a microfiber.

6. The method of claim 1, wherein the cleaning mop is allowed to dry after the additive is applied, wherein said aqueous floor disinfecting composition is then applied to the cleaning mop.

* * * * *